United States Patent [19]

Sezginer et al.

[11] Patent Number: 5,629,623
[45] Date of Patent: May 13, 1997

[54] PULSED NUCLEAR MAGNETISM TOOL FOR FORMATION EVALUATION WHILE DRILLING

[75] Inventors: Abdurrahman Sezginer, Brookfield; Robert L. Kleinberg, Ridgefield, both of Conn.

[73] Assignee: Schlumberger Technology Corporation, Ridgefield, Conn.

[21] Appl. No.: 338,317

[22] Filed: Nov. 14, 1994

Related U.S. Application Data

[63] Continuation-in-part of Ser. No. 200,815, Feb. 22, 1994, abandoned, which is a continuation of Ser. No. 922,254, Jul. 30, 1992, abandoned.

[51] Int. Cl.⁶ ............................................. G01R 33/20
[52] U.S. Cl. ............................................. 324/303
[58] Field of Search ............................ 324/300, 303, 324/306, 356, 369, 338

[56] References Cited

U.S. PATENT DOCUMENTS

| | | | |
|---|---|---|---|
| 3,617,867 | 11/1971 | Herzog | 324/303 |
| 3,777,560 | 12/1973 | Guignard | 73/151.5 |
| 4,350,955 | 9/1982 | Jackson et al. | 324/303 |
| 4,479,564 | 10/1984 | Tanguy | 367/35 |
| 4,536,714 | 8/1985 | Clark | 324/338 |
| 4,629,986 | 12/1986 | Clow et al. | 324/303 |
| 4,710,713 | 12/1987 | Strikman | 324/303 |
| 4,714,881 | 12/1987 | Givens | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,792,757 | 12/1988 | Vail, III et al. | 324/303 |
| 4,899,112 | 2/1990 | Clark et al. | 324/338 |
| 4,933,638 | 6/1990 | Kenyon et al. | 324/303 |
| 4,933,640 | 6/1990 | Kuckes | 324/346 |
| 4,949,045 | 8/1990 | Clark et al. | 324/338 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |
| 5,138,263 | 8/1992 | Towle | 324/338 |
| 5,235,285 | 8/1993 | Clark et al. | 324/342 |
| 5,280,243 | 1/1994 | Miller | 324/303 |
| 5,363,041 | 11/1994 | Sezginer | 324/303 |

*Primary Examiner*—Sandra L. O'Shea
*Assistant Examiner*—Raymond Y. Mah
*Attorney, Agent, or Firm*—Brigitte L. Jeffery; Leonard W. Pojunas; Keith G. W. Smith

[57] ABSTRACT

A permanent magnet of a pulsed nuclear magnetic resonance (NMR) device is positioned within a drill collar for evaluating earth formations. In this way, the torsional and bending strengths of the drill collar are maximized with relatively little sacrifice of the magnetic moment of the permanent magnet. The resulting tool makes NMR measurements while the formation is being drilled. An antenna for producing and detecting an oscillating RF field in the earth formation is either located in a groove in the outer surface of the drill collar, or in an alternative embodiment, the drill collar itself serves as an RF antenna.

10 Claims, 6 Drawing Sheets

PULSED NUCLEAR MAGNETISM TOOL FOR FORMATION EVALUATION WHILE DRILLING

This is a continuation-in-part of application Ser. No. 200,815, filed Feb. 22, 1994, abandoned, which is a continuation of application Ser. No. 922,254, filed Jul. 30, 1992, now abandoned. Cross reference is made to co-pending application Ser. No. 08/623,031 filed on Mar. 28, 1996, which is a divisional of U.S. application Ser. No. 08/337,784, filed on Nov. 14, 1994, now abandoned, which is a continuation-in-part of U.S. application Ser. No. 08/200,815, filed Feb. 22, 1994, abandoned, which is a continuation of U.S. application Ser. No. 07/922,254, filed Jul. 30, 1992, abandoned.

FIELD OF THE INVENTION

The invention concerns a tool for logging while drilling. More specifically the invention concerns a tool for logging a formation using pulsed nuclear magnetic resonance (NMR) techniques while drilling a borehole into the formation.

BACKGROUND OF THE INVENTION

Several pulsed NMR tools have been designed for borehole deployment via wireline and are described in U.S. Pat. Nos:

4,350,955, issued 9/1982 to Jackson et al.;
4,629,986, issued 12/1986 to Clow et al.;
4,710,713, issued 12/1987 to Strikman;
4,717,876, issued 1/1988 to Masi et al.;
4,717,877, issued 1/1988 to Taicher et al.;
4,717,878, issued 1/1988 to Taicher et al.;
4,714,881, issued 12/1987 to Givens;
5,023,551, issued 6/1991 to Kleinberg et al.;
5,055,787, issued 10/1991 to Kleinberg et al.; and
5,055,788, issued 10/1991 to Kleinberg et al.

All of these patents describe NMR tools which employ permanent magnets to polarize hydrogen nuclei, and RF antennas to excite and detect nuclear magnetic resonance to determine porosity, free fluid ratio, or permeability of a formation, for example. The tools described in U.S. Pat. Nos. 4,717,877; 5,055,787; and 5,055,788 have been successfully tested in boreholes.

The instrument concepts described in the related U.S. Pat. Nos. 4,710,713 and 4,717,877 have a rotationally invariant region of resonance, which is a thin cylindrical shell coaxial with the borehole. The electromagnetic fields have a simple azimuthal dependence: both the static and RF fields at any point in the vicinity of the instrument rotate at the same rate as the instrument rotates. The rotation does not disturb the NMR measurement because the nuclear magnetic moment adiabatically tracks the magnetic field. The radial thickness of the resonance region of these instruments is on the order of 1 mm.

The instrument concepts described in the related U.S. Pat. Nos. 4,350,955, 4,629,986, and 4,717,876 have rotationally invariant static and RF fields and a relatively large resonant region (at least 10 mm thick). The resonant region is thicker because the magnitude of the magnetic field is stationary at the resonant region. These patents, however, do not describe rotating the instruments.

Several logging while drilling (LWD) and measuring while drilling (MWD) tools have been designed for formation evaluation while drilling and drill string characterization while drilling, respectively. Logging or measuring instruments are placed in drill collars up to 100 ft behind the drill bit. An MWD tool is described in U.S. Pat. Nos. 3,777,560 to Guignard and 4,479,564 to Tanguy. An LWD tool is described in U.S. Pat. Nos. 4,899,112 to Clark et al. and 4,949,045 to Clark et al. Typically, these tools use electromagnetic techniques in evaluating resistivity of a formation while drilling.

None of the NMR tools have been used in a drilling string, nor have the LWD or MWD tools used pulsed NMR techniques.

SUMMARY OF THE INVENTION

One aspect of the invention concerns an apparatus comprising a drilling means for drilling a borehole in an earth formation; and a measuring means, connected to the drilling means, for making nuclear magnetic resonance (NMR) measurements while the borehole is being drilled. A measuring means is connected to the drilling means, for making nuclear magnetic resonance (NMR) measurements while the borehole is being drilled. The measuring means comprises: a) means, mounted within the drill collar, for producing a static magnetic field through the drill collar and into the formation; b) a drill collar per se or means mounted to the drill collar for producing an oscillating magnetic field into the formation to excite nuclei of materials in the formation; and c) means for detecting resulting signals induced in the formation and determining a property of the formation in light of the detected signals.

In a preferred embodiment, the invention concerns a drill string and bit for drilling a borehole in an earth formation and a pulsed NMR device which is housed by the drill string. The embodiment includes a channel within the drill string and pulsed NMR device through which drilling mud is pumped into the borehole. The pulsed NMR device comprises a tubular magnet which is mounted within the drill string to surround the channel. The pulsed NMR device also includes an antenna mounted in an axial recess in the exterior surface of the drill string or uses the drill collar as an RF antenna. Thus, the tool logs the earth formation using pulsed NMR techniques while the tool drills a borehole into the formation.

DETAILED DESCRIPTION

U.S. Pat. No. 5,280,243 to Miller et al. describes a Nuclear Magnetic Resonance (NMR) logging while drilling tool. According to this patent, sensor components (the RF coil and ceramic magnet) are enclosed behind a 1 m long (approximately), 360° cover made of a nonmetallic material. Although this cover is stood off from the formation by stabilizer blades immediately above and below the tool, field experience indicates that such a cover will be ground away rapidly by the cuttings made by the drill bit. These formation cuttings are carded by drilling muds up the borehole and past the cover during the drilling process. In addition, torsional and bending forces are born by a steel collar section 42 inside the magnet 46. This configuration limits the outer radius of the collar section, hence its torsional and bending strength.

Since the torsional and bending strengths of a shaft are proportional to the fourth power of its radius, whereas the magnetic moment of a cylindrical magnet is proportional to the second power of its radius, the inventors have found that it is imperative to place the magnet of an LWD NMR tool inside the drill collar (the load bearing member). The maximum permissible magnet volume is larger if the magnet is placed inside the drill collar. Various means are described for placing the magnet inside the drill collar.

Figure 1:
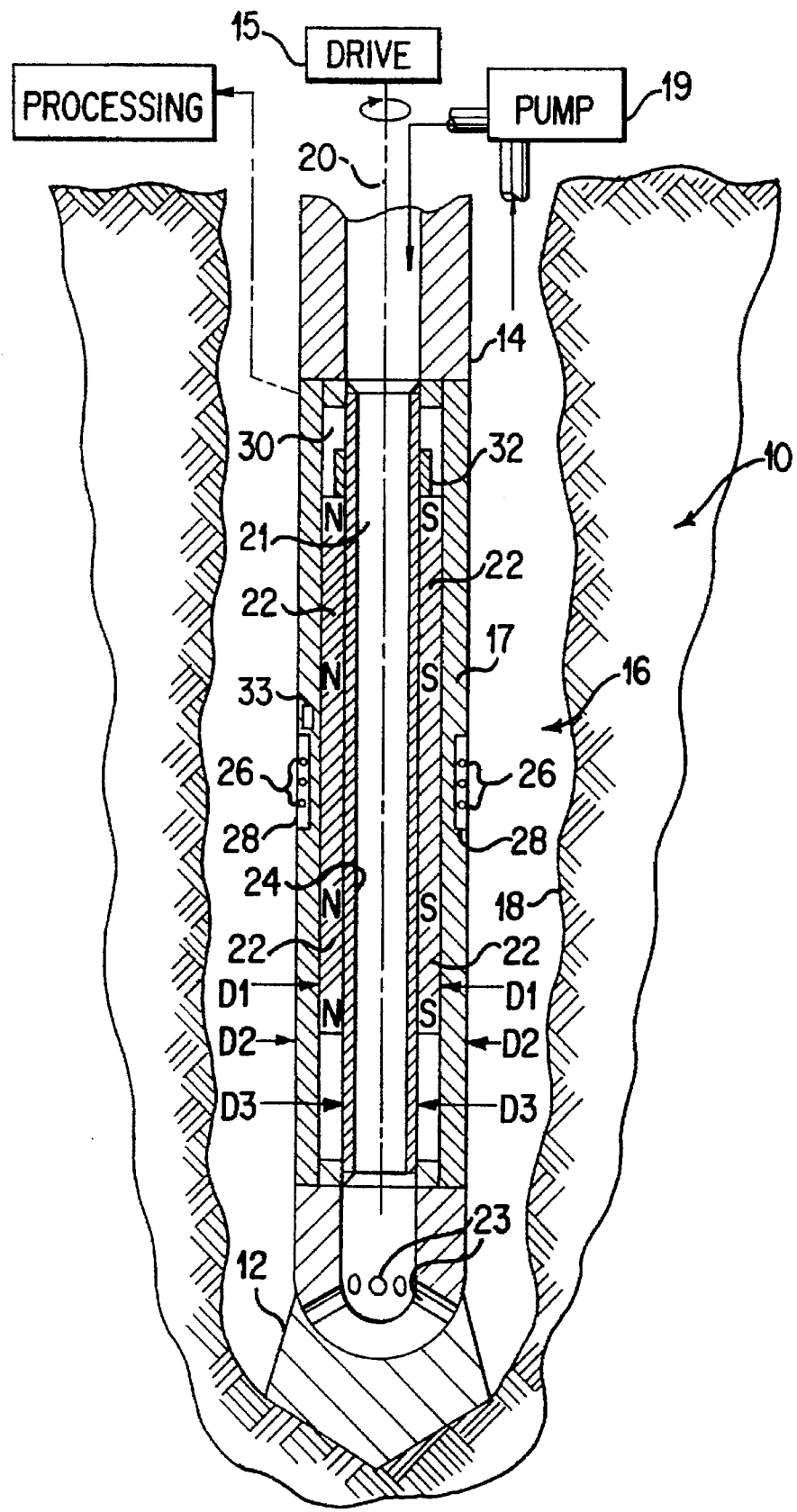
FIG. 1 shows a cross section of a tool for pulsed NMR formation evaluation while drilling.

FIG. 1 shows a tool 10 according to this invention. The tool 10 includes a drill bit 12, drill string 14, and pulsed NMR device 16 (housed within a drill collar 17). The drill bit 12 and drill string 14 comprise a means for drilling a borehole 18 in an earth formation. The drill collar 17 is a strong shaft that bears the torque, bending moment, and axial force on the drill string. It is also the external member that is in contact with the drilling fluid and rock cuttings in the well bore, and the earth formation in which the well is drilled. A drive mechanism 15 rotates the drill string 14 and drill bit 12 as is known in the art. See U.S. Pat. No. 4,949,045 to Clark et al., for example. The drill collar 17 is made of a nonmagnetic alloy. The tool 10 also comprises a means for making pulsed nuclear magnetic resonance (NMR) measurements while a borehole 18 is being drilled. The pulsed NMR device 16 is connected as part of the drill string 14 and is housed within the drill string 14.

The borehole 18 typically contains fluid, such as drilling muds which are pumped by pump 19 into the borehole 18 from and back to the surface to carry away formation cuttings back to the surface. Such a pump is described in U.S. Pat. No. 4,949,045 to Clark et al., for example. A channel 21 within the drill string 14 comprises a means for carrying the borehole fluid through the drill string 14. The channel 21 is cut within the drill collar 17 substantially parallel to the longitudinal axis 20. The channel 21 opens to the borehole 18 through ports 23 in the drill bit 12.

The pulsed NMR device 16 comprises, in a preferred embodiment, tubular magnet 22 arranged and housed in the drill string 14 and within the pulsed NMR device 16 to surround the channel. The sleeve shaped, tubular magnet 22 is permanently magnetized transversely to the axis of the tool. The magnet 22 is located inside the drill collar 17 and outside a mud sleeve 24. Its length is approximately 2–6 ft. The magnet 22 can be installed into a recess that is cut out either from the outside or from the inside of the drill collar 17. Cutting from the inside is preferred because the bending and torsional strengths of the drill collar 17 are proportional to the difference of the fourth powers of the drill collar's outer and inner radii. For example, in FIG. 1 the inner D1 and outer D2 diameters of the drill collar 17 at the magnet-recess are 5.000" and 6.750", respectively. The inner D3 and outer D1 diameters of the magnet 22 are 3.000" and 5.000", respectively. These dimensional values, and those below, are only cited as examples. Numerous other values of the diameters, thickness, and depth are possible.

The magnet 22 is protected from the pressure and abrasion of drilling mud by a 0.375" thick nonmagnetic steel mud sleeve 24 inside the drill collar 17, for example. The mud sleeve 24 defines the channel 21 and is positioned to isolate the tubular magnet 22 from the drilling mud comprising the borehole fluid. Had the recess for the magnet 22 been made from outside surface of the drilling collar 17, the recess would have to be at most 0.276" deep, for example, in order to achieve the same mechanical strength. This shallow recess must be considered in accommodating the magnet 22 and the protective mud sleeve 24. The inventors have found it is preferable to cut the recess for the magnet 22 from the inside of the drill collar 17 to obtain greater mechanical strength and sufficient space to accommodate the magnet 22 and steel mud sleeve 24. The magnet can be clamped in position relative to the mud sleeve 24 and drill collar 17.

FIG. 1 also shows an RF antenna 26 located in an antenna recess 28 adjacent the tubular magnet 22. The pulsed NMR portion 16 of this tool 10 comprises the antenna 26 mounted on the drill collar 17 and the tubular magnet 22 mounted within the drill collar 17. The antenna 26 is mounted in an exterior recess 28 of an exterior surface of the drill collar 17. The antenna recess 28 is preferably on the outside of the drill collar 17, because at the frequency of operation (0.1–2 MHz) the resulting RF magnetic field could not diffuse out through the drill collar 17.

Figure 10:
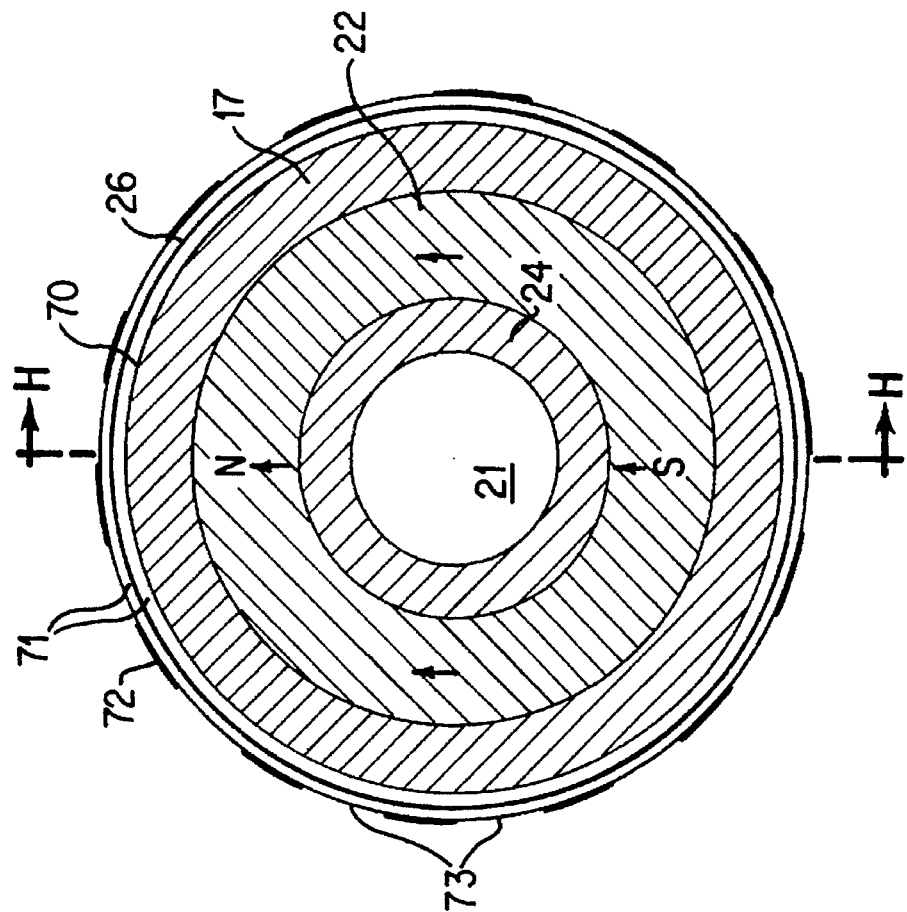
FIGS. 9 and 10 show another embodiment of the invention.
Figure 9:
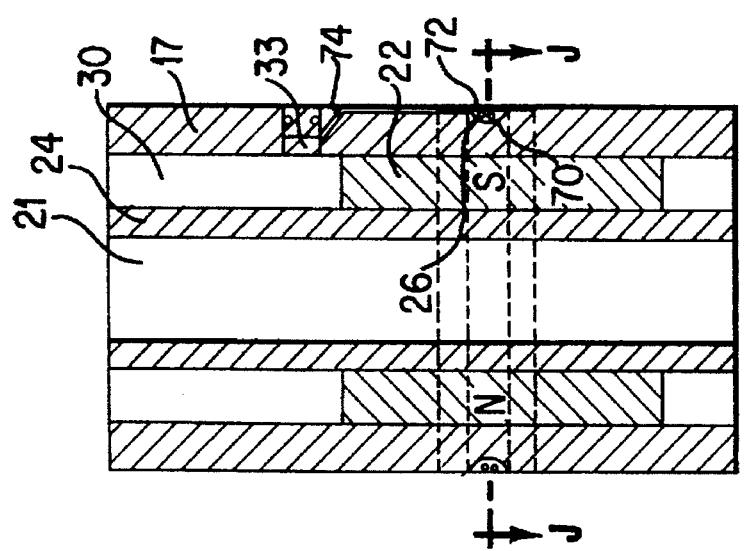

The antenna 26 can also run axially along the drill collar (See FIG. 3), but can comprise a coil which surrounds the channel, mud sleeve 24 and magnet 22 (See FIGS. 1 and 9). The antenna recess 28 of FIG. 3, for example, is preferably filled with a nonconducting material such as ceramic, plastic or rubber as discussed below. In the case of FIGS. 12, 3, 9 and 10, the antenna recess 28 can also be filled with a ferrite to improve the efficiency of the RF antenna 26. In the case of FIGS. 9 and 10, the RF antenna 26 can be protected by a sheet-metal shield with axial slots to let out the RF magnetic field. In the case of FIGS. 4–7, the antenna can be protected by a sheet-metal shield with slots transverse to the axis of the tool. The slotted shield is mounted in the recess 28 and radially outside the antenna 26. Examples of the construction of the antenna and the slotted shield have been described in the U.S. Pat. No. 4,949,045 to Clark et al. issued August 1990 in the context of a Compensated Dual Resistivity Tool (mark of Schlumberger Technology Corporation), and U.S. Pat. No. 4,536,714 to Clark issued August 1985.

The pulsed NMR portion 16 of this tool 10 also includes electronic circuitry. The drill collar 17 includes a compartment 30 preferably at atmospheric-pressure, which contains circuitry 32. Compartment 30 can be located either in an annulus between the drill collar 17 and the mud sleeve 24 as shown in FIG. 1, or it can be located in a sub in the mud channel 21. This driving circuitry 32 is similar to that disclosed in the two U.S. Pat. Nos. to Kleinberg et at., 5,055,787 and 5,055,788. The drill-collar 17 also includes a small compartment 33 preferebly at atmospheric pressure, which contains means of connecting the antenna 26 to the electronics 32. The compartment 33 can also contain electronic components, such as tuning capacitors, Q-switch, duplexer, and preamplifier, which are preferably placed close to the RF antenna. Such components are described in the Kleinberg et at. patents.

The NMR device 16 is pulsed and the formation is logged according to the technique described in U.S. Pat. Nos. 5,055,787; 5,055,788; and 5,023,551 to Kleinberg et al, U.S. Pat. No. 5,363,041 to Sezginer, and co-pending application Ser. No. 800,339. The information representing the evaluation of the formation is stored in a downhole memory (not shown) and is obtained from the pulsed NMR device 16 in a manner as described in U.S. Pat. No. 4,949,045 to Clark et al.

Figure 2:
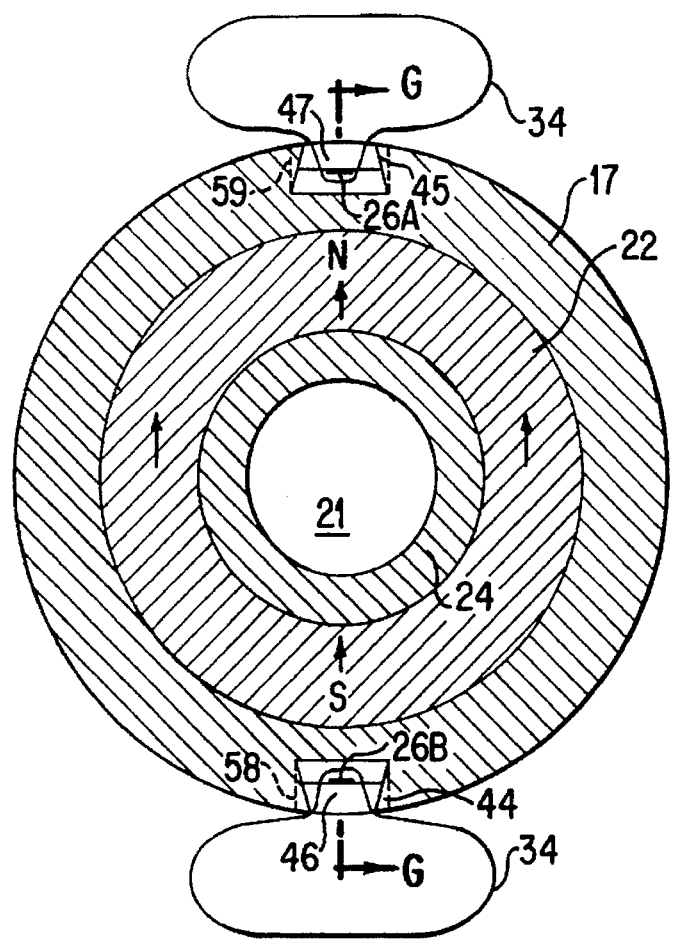
FIGS. 2 and 3 show one embodiment of the invention.
Figure 3:
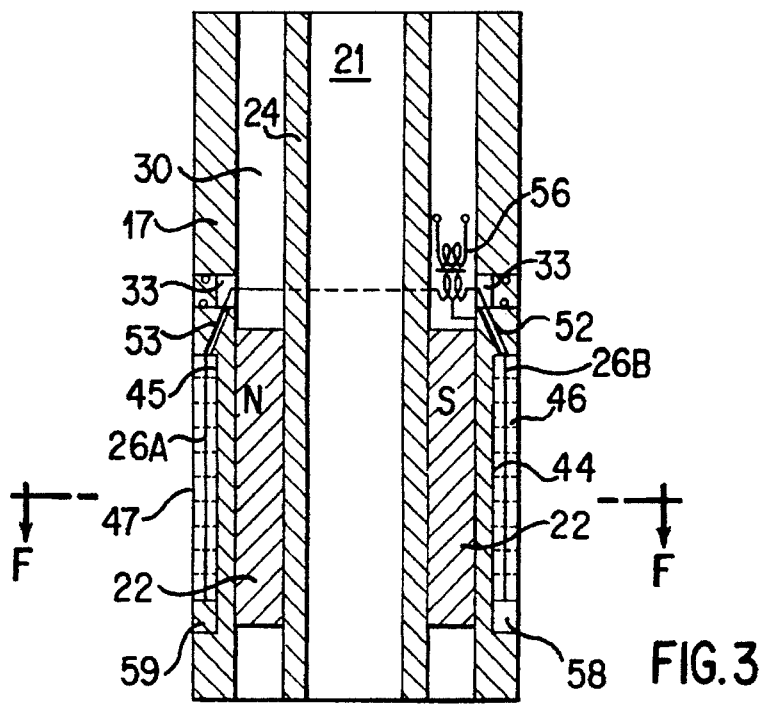
Figure 4:
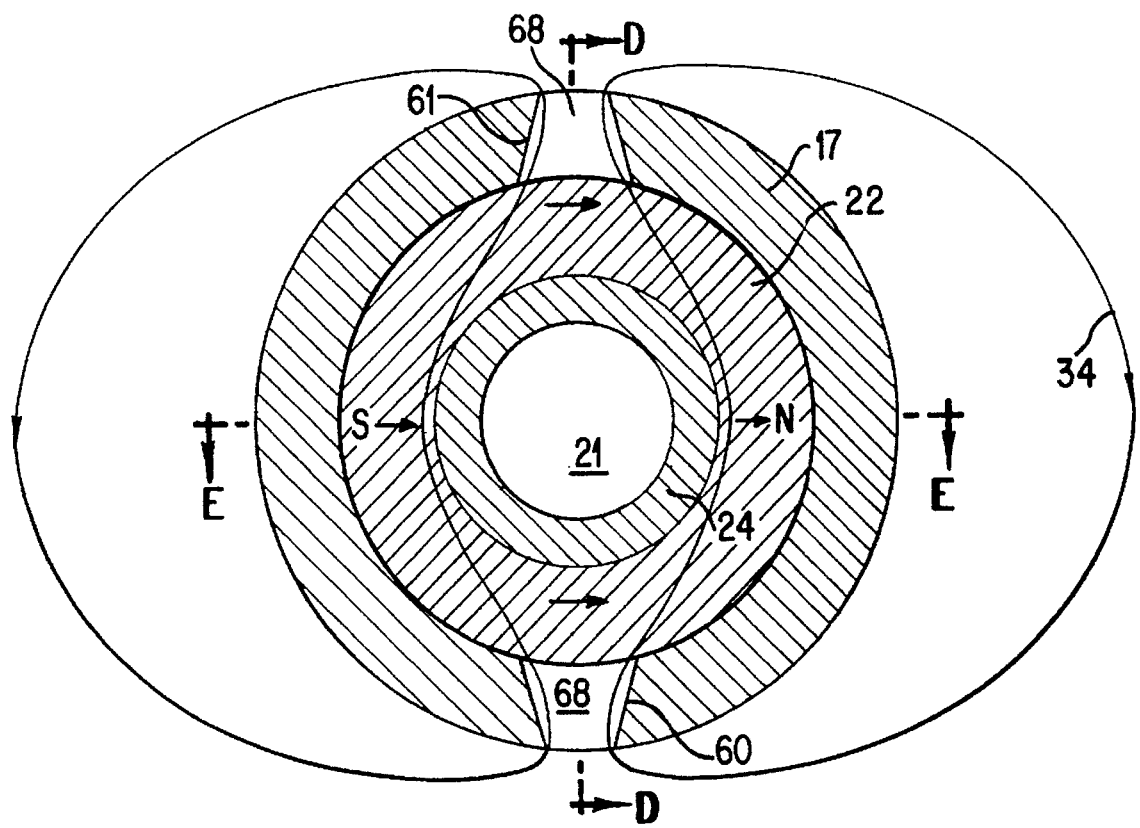
FIGS. 4–8 show another embodiment of the invention.
Figure 5:
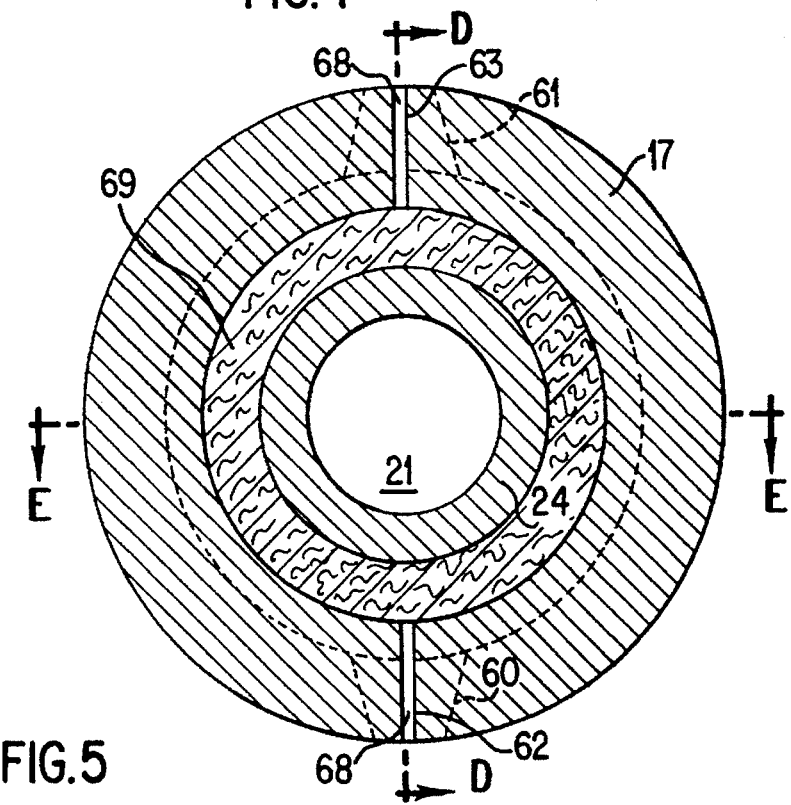
Figure 6:
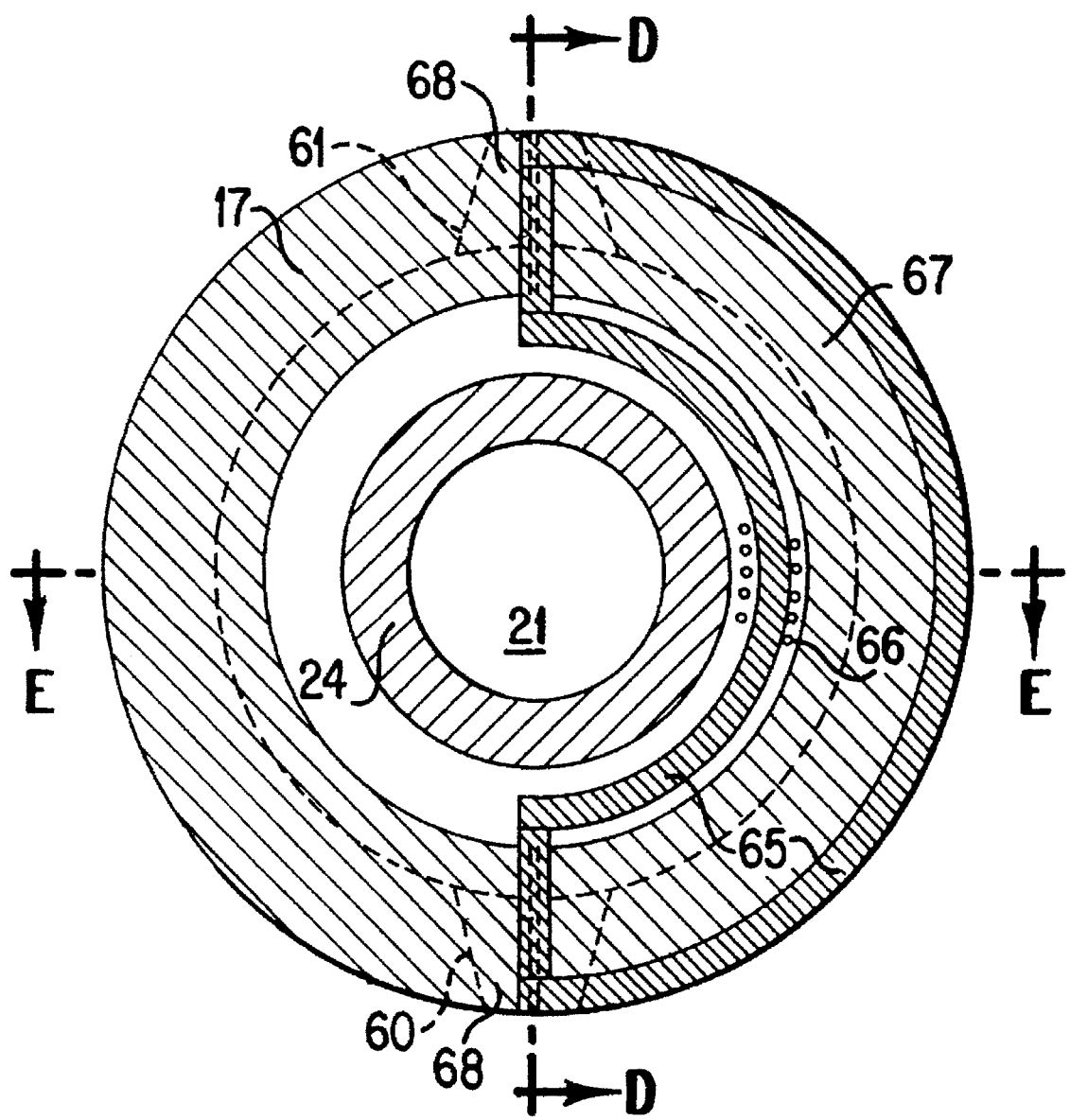
Figure 8:
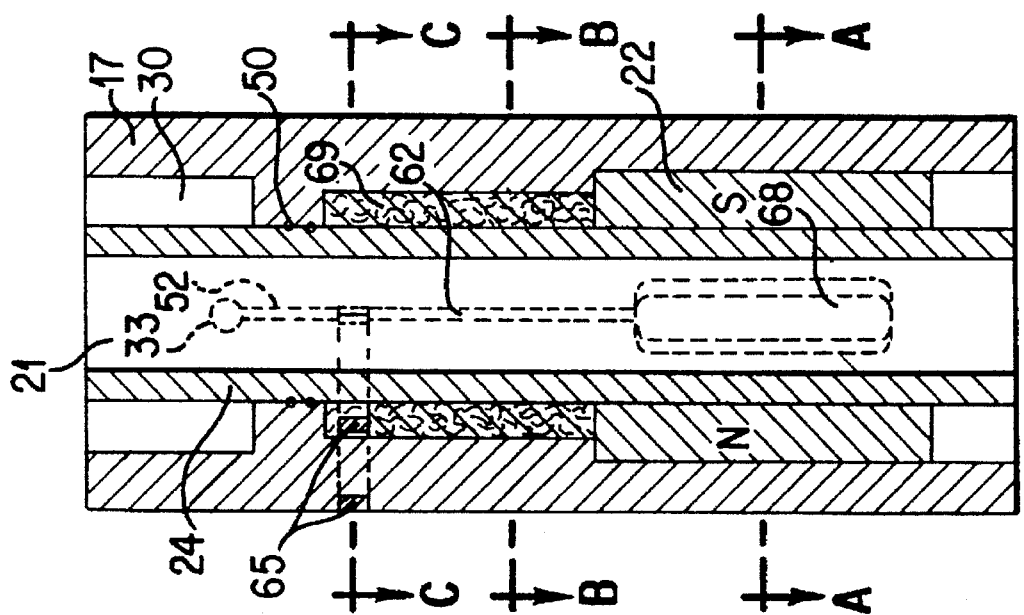
Figure 7:
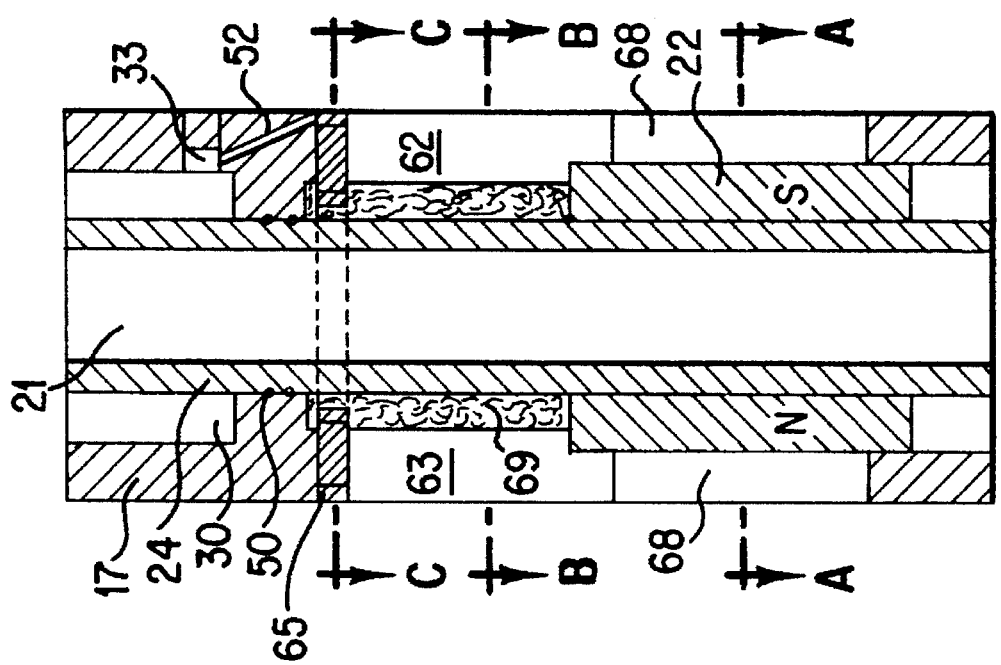

FIGS. 2 and 3 show one embodiment of the invention. The drill collar 17 entirely encloses the magnet 22. The magnet 22 does not interfere with the RF field 34 produced by antenna 26. Therefore, the magnet 22 can be either ceramic or metallic. Since magnets made of metallic materials such as Sm-Co or Nd-Fe-B are 2.5 times stronger than ceramic magnets, they can be made thinner in the radial dimension, thus simplifying mechanical design. Conductors 26A, 26B in axial grooves 44, 45 cut into the outside surface of the drill collar 17 make up the RF coil. The RF conductors 26A, 26B and their grooves 44, 45 are shorter than the magnet 22 so that the conductors 26A, 26B have negligible sensitivity to the spins in the fringing field of the magnet 22 where the resonant region intersects the borehole. The RF conductors 26A, 26B are protected from the drilling environment by nonconductive, nonmagnetic covers 46,47. Ceramic is a suitable material for the nonmagnetic covers 46, 47.

Magnitudes of and the angle between the RF field and static field do not change on any imaginary cylindrical surface coaxial with the axis 20 of the tool when both fields are dipolar. Thus, the RF magnetic field, in this sense is substantially symmetric about the longitudinal axis of the logging tool. This symmetry is needed because the tool is rotating while drilling. More than two axial grooves (44, 45) may be needed in the drill collar 17 to make the RF field of antenna 26 closer to a two-dimensional dipolar field.

FIG. 3 illustrates practical details of this embodiment. They are not fundamental to the design concept and can be implemented by means other than described here.

The conductors 26A, 26B are electrically grounded to the drill collar 17 at one end. At the other end, the conductors 26A, 26B are connected to an RF transformer 56 via pressure feed-throughs 52, 53. The transformer 56 keeps a 180° phase difference between the currents in diametrically opposite RF conductors. If the transformer 56 has a magnetic core, the transformer 56 must be located sufficiently far away from the magnet 22 so that the core of the transformer 56 is not magnetically saturated and so that the transformer 56 does not perturb the field of the magnet. Alternatively, the transformer 56 can be implemented using active circuits without any magnetic components.

The ceramic covers 46, 47 of the RF antenna 26 are segmented. These segments are slid into corresponding dove-tail shaped grooves (44, 45 of FIG. 2) from the pits 58, 59. Pits 58, 59 are later covered by metallic inserts bolted into place. The RF antenna 26 can be impregnated by a rubber compound to seal out the borehole fluid. The RF antenna 26 is exposed to the borehole pressure. The magnet 22 and transformer 56 are at atmospheric pressure.

FIGS. 4-8 illustrate another embodiment of the invention. According to this embodiment, the drill collar itself produces the oscillating magnetic field. The RF field 34 is produced outside the drill collar 17 by making the drill collar 17 into an antenna comprising a single-turn coil or loop. This is accomplished by cutting axially oriented slots 60, 62, 61 and 63 through the entire thickness of the drill collar 17 as shown in FIGS. 4-7. The loop formed by the drill collar 17 cannot be broken to make electrical contacts to the drill collar because this would diminish the strength of the drill collar 17. Therefore, a toroidal magnetic core 65 (See FIG. 6) driven by a primary winding 66 is wrapped around one leg 67 of the split drill collar 17 to induce an RF current in the antenna formed by the drill collar 17.

Effectively, this arrangement is a voltage transformer where the magnetic core 65 is the core, a portion of the drill collar 17 is the secondary winding, and 66 is the primary winding. The transformer is a means for inducing an RF current on the drill collar. This induced current circulates at the surface of the drill collar 17, mainly around the slot 60, 62 and the slot 61, 63. As is evident from FIG. 6, a portion of the magnetic core is inside the drill collar and a portion of the magnetic core is outside the drill collar. The magnetic core 65 is located sufficiently far away from the magnet 22, for example by a fiberglass spacer 69, so that the magnetic core 65 is not magnetically saturated and the field of the magnet 22 is not significantly perturbed by the presence of the magnetic core 65.

An example of such transformer technology is described in U.S. Pat. No. 5,235,285 to Clark et al. The Clark patent describes a toroidal coil having leads for sensing current flow. The leads of the coil pass through a bulkhead feedthrough to circuitry. One lead or conductor is coupled to an amplifier and the other lead or conductor is coupled to a drill collar. See FIGS. 3, 5, and 6 of the Clark patent, for example.

The slots 62, 63 are narrower than the slots 60, 61 to keep the RF field low in the fringing field of the magnet 22. Slots 60-63 can be filled by ceramic insulating blocks 68. The magnet and all components of the RF winding 66 (including the slotted drill collar 17) are exposed to the borehole pressure. The RF winding 66 is connected to the RF electronics via a pressure feed-through 52. Since the RF field has to go through the magnet 22 in this embodiment, the magnet 22 must be made of a nonconductive material such as ceramic.

FIGS. 9 and 10 illustrate another embodiment of the invention. According to this embodiment, the construction of the RF coil 26 can also be similar to the antennas used in the Compensated Dual Resistivity (CDR) tool of Schlumberger, as shown in FIG. 9. The RF coil 26 is wound around the drill collar 17 in a groove 70 cut circumferentially outside the drill collar 17. Both the groove 70 and the coil 26 are transverse to the axis of the collar 17. The coil 26 is embedded in fiberglass 71 (See FIG. 10) and covered by a metallic shield 72. Vertical slots 73 cut through the shield 72 let the RF magnetic field through to the formation. The RF coil 26, which is exposed to the borehole pressure, is electrically connected to RF circuitry inside the drill collar 17 via a pressure feed-through 74. The magnet 22, totally enclosed inside the drill collar 17, can be at atmospheric pressure and it can be either metallic or ceramic because it does not interfere with the RF field of the coil 26.

Means of securing the mud sleeve 24 to the drill collar 17 and establishing a sealed region between the drill collar and the mud sleeve are known in the art and are not shown in FIGS. 1-10.

Because the resonance region of the instruments of U.S. Pat. Nos. 4,710,713 and 4,717,877 is on the order of 1 mm, it is expected that lateral vibrations of a drill collar which might be proposed for containing an NMR device would adversely affect an NMR measurement. For example, a lateral, 50 Hz vibration of 1 mm amplitude (100 g acceleration) would disable the measurement. Also, the inventors have determined that, since the drill string makes several revolutions in the duration of a pulsed NMR measurement (on the order of 1 second), an NMR instrument in a drilling string must be rotationally symmetric. In addition, a CPMG sequence for tolerating vibration of the tool while drilling is described in U.S. patent application Ser. No. 08/623,031 filed on Mar. 28, 1996, which is a divisional of U.S. application Ser. No. 08/337,784 filed Nov. 14, 1994, now abandoned, which is a continuation-in-part of U.S. application Ser. No. 08/200,815, filed Feb. 22, 1994, abandoned, which is a continuation of U.S. application Ser. No. 07/922,254, filed Jul. 30, 1992, abandoned.

We claim:

1. A method comprising:

drilling a borehole in an earth formation; and making nuclear magnetic resonance (NMR) measurements while the borehole is being drilled, including:
   a) producing a static magnetic field from within a drill collar and into the formation;
   b) producing an oscillating magnetic field from the drill collar into the formation to excite nuclei of materials in the formation; and
   c) detecting resulting signals induced in the formation and determining a property of the formation in light of the detected signals.

2. An apparatus comprising:
   a drilling means for drilling a borehole in an earth formation; and
   a measuring means, connected to the drilling means, for making nuclear magnetic resonance (NMR) measurements while the borehole is being drilled, the measuring means comprising:
   a) means, mounted within the drilling means, for producing a static magnetic field through the drilling means and into the formation;
   b) a portion of the drilling means arranged to produce an oscillating magnetic field into the formation to excite nuclei of materials in the formation; and
   c) means for detecting resulting signals induced in the formation and determining a property of the formation in light of the detected signals.

3. The apparatus of claim 2, wherein the drilling means includes a drill collar which produces the oscillating magnetic field.

4. The apparatus of claim 3, comprises a winding mounted inside the drill collar, the winding carries an RF signal, and the winding also comprises a means for inducing an RF current on the drill collar.

5. The apparatus of claim 4, wherein the means for inducing the RF current includes a magnetic core connected such that the winding forms a primary winding and the portion of the drill collar forms a secondary winding of a voltage transformer.

6. The apparatus of claim 5, wherein a portion of the magnetic core is inside the drill collar and a portion of the magnetic core is outside the drill collar.

7. An apparatus comprising:
   a drilling means for drilling a borehole in an earth formation; and
   a measuring means, connected to the drilling means, for making nuclear magnetic resonance (NMR) measurements while the borehole is being drilled, the measuring means comprising:
   a) means for producing a static magnetic field in the formation;
   b) means, mounted inside the drilling means connected such that the drilling means produces an oscillating magnetic field into the formation to excite nuclei of materials in the formation; and
   c) means for detecting resulting signals induced in the formation and determining a property of the formation in light of the detected signals.

8. An apparatus comprising:
   a drilling means for drilling a borehole in an earth formation; and,
   a measuring means, connected to the drilling means, for making nuclear magnetic resonance (NMR) measurements while the borehole is being drilled, the measuring means comprising:
   a) means, mounted to the drilling means, for producing a static magnetic field into the formation;
   b) a portion of the drilling means arranged to produce an oscillating magnetic field into the formation to excite nuclei of materials in the formation; and,
   c) means for detecting resulting signals induced in the formation and determining a property of the formation in light of the detected signals.

9. The apparatus of claim 2, wherein the drilling means includes a drill collar which produces the oscillating magnetic field.

10. A method comprising:
    drilling a borehole in an earth formation;
    making nuclear magnetic resonance (NMR) measurements while the borehole is being drilled;
    producing a static magnetic field into the formation;
    producing an oscillating magnetic field with the drill collar and into the formation to excite nuclei of materials in the formation; and,
    detecting resulting signal induced in the formation and determining a property of the formation in light of the detected signals.

* * * * *